United States Patent
Bielenstein et al.

(10) Patent No.: US 9,999,459 B2
(45) Date of Patent: Jun. 19, 2018

(54) VACUUM MIXING DEVICE FOR BONE CEMENT AND METHOD FOR MIXING BONE CEMENT IN SAID DEVICE

(71) Applicant: Stryker European Holdings I, LLC, Kalamazoo, MI (US)

(72) Inventors: Oliver Bielenstein, Berlin (DE); Christoph Sattig, Dieburg (DE); Stefan Deusser, Karlstein (DE); Volker Stirnal, Dieburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 295 days.

(21) Appl. No.: 14/880,398

(22) Filed: Oct. 12, 2015

(65) Prior Publication Data

US 2016/0045242 A1 Feb. 18, 2016

Related U.S. Application Data

(63) Continuation of application No. 13/257,031, filed as application No. PCT/EP2010/001665 on Mar. 17, 2010, now Pat. No. 9,186,635.

(30) Foreign Application Priority Data

Mar. 17, 2009 (DE) .......................... 10 2009 013 211

(51) Int. Cl.
*A61B 17/88* (2006.01)
*B01F 15/02* (2006.01)
(Continued)

(52) U.S. Cl.
CPC .......... *A61B 17/8833* (2013.01); *B01F 7/007* (2013.01); *B01F 15/0212* (2013.01);
(Continued)

(58) Field of Classification Search
CPC ............ A61B 17/8825; A61B 17/8827; A61B 17/8833; A61B 2017/8838;
(Continued)

(56) References Cited

U.S. PATENT DOCUMENTS 1,680,616 A 8/1928 Horst
1,744,893 A 1/1930 Hein
(Continued)

FOREIGN PATENT DOCUMENTS

DE 60012383 T2 9/2005
DE 69634704 T2 3/2006
(Continued)

OTHER PUBLICATIONS

International Search Report issued in PCT/EP2010/001665 dated Jul. 20, 2010.
(Continued)

*Primary Examiner* — Tony G Soohoo
(74) *Attorney, Agent, or Firm* — Lerner, David, Littenberg, Krumholz & Mentlik, LLP

(57) ABSTRACT

The application relates to a vacuum mixing device for bone cement, where the monomer is pressed into a mixing container due to the surrounding vacuum and a gas volume present in the monomer container.

20 Claims, 6 Drawing Sheets

(51) Int. Cl.
  *B01F 7/00* (2006.01)
  *A61B 90/00* (2016.01)
(52) U.S. Cl.
  CPC ...... *B01F 15/0223* (2013.01); *B01F 15/0258* (2013.01); *A61B 17/8825* (2013.01); *A61B 17/8827* (2013.01); *A61B 2017/8838* (2013.01); *A61B 2090/037* (2016.02); *B01F 15/0279* (2013.01); *B01F 2015/0273* (2013.01)
(58) Field of Classification Search
  CPC ........... A61B 2090/037; B01F 15/0212; B01F 15/0223; B01F 15/0258; B01F 15/0279; B01F 2015/0273; B01F 7/007
  See application file for complete search history.

(56) References Cited

U.S. PATENT DOCUMENTS

| | | |
|---|---|---|
| 2,425,093 A | 8/1947 | Fosler |
| 2,638,022 A | 5/1953 | Reyes |
| 3,036,819 A | 5/1962 | Edwin |
| 3,228,565 A | 1/1966 | Stanzel |
| 3,506,006 A | 4/1970 | Lange, Jr. |
| 3,654,926 A | 4/1972 | Rietman |
| 3,702,609 A * | 11/1972 | Steiner ............... A61M 5/2033 604/139 |
| 3,739,947 A | 6/1973 | Baumann et al. |
| 3,742,988 A | 7/1973 | Kush |
| 3,869,315 A | 3/1975 | Dolgner |
| 3,872,867 A | 3/1975 | Killinger |
| 3,892,237 A * | 7/1975 | Steiner ............... A61M 5/2053 604/157 |
| 3,945,382 A | 3/1976 | Ogle |
| 3,983,994 A | 10/1976 | Wyslotsky |
| 3,986,838 A | 10/1976 | Reichert |
| 3,995,630 A | 12/1976 | van de Veerdonk et al. |
| 4,043,335 A | 8/1977 | Ishikawa |
| 4,178,928 A | 12/1979 | Tischlinger |
| 4,180,070 A | 12/1979 | Genese |
| 4,185,582 A | 1/1980 | Bryant |
| 4,218,525 A | 8/1980 | Selgin |
| 4,227,528 A | 10/1980 | Wardlaw |
| 4,241,850 A | 12/1980 | Speer et al. |
| 4,246,229 A | 1/1981 | McBride et al. |
| 4,272,479 A | 6/1981 | Huneke et al. |
| 4,298,777 A | 11/1981 | Bryant |
| 4,306,554 A | 12/1981 | Schwartz et al. |
| 4,312,344 A | 1/1982 | Nilson |
| 4,328,754 A | 5/1982 | Goodman |
| 4,340,007 A | 7/1982 | Hogan |
| 4,375,504 A | 3/1983 | Jensen et al. |
| 4,423,724 A | 1/1984 | Young |
| 4,453,934 A | 6/1984 | Gahwiler et al. |
| 4,463,875 A | 8/1984 | Tepic |
| 4,465,183 A | 8/1984 | Saito et al. |
| 4,467,588 A | 8/1984 | Carveth |
| 4,483,049 A | 11/1984 | Gustavsson et al. |
| 4,505,433 A | 3/1985 | Selenke |
| 4,515,586 A | 5/1985 | Mendenhall et al. |
| 4,526,758 A | 7/1985 | Alengoz et al. |
| 4,528,268 A | 7/1985 | Andersen et al. |
| 4,533,641 A | 8/1985 | Holt |
| 4,676,406 A | 6/1987 | Frischmann et al. |
| 4,676,655 A | 6/1987 | Handler |
| 4,693,706 A | 9/1987 | Ennis, III |
| 4,743,229 A | 5/1988 | Chu |
| 4,757,916 A | 7/1988 | Goncalves |
| 4,799,801 A | 1/1989 | Bruning |
| 4,801,009 A | 1/1989 | Amos |
| 4,808,184 A | 2/1989 | Tepic |
| 4,865,189 A | 9/1989 | Guerra et al. |
| 4,936,446 A | 6/1990 | Lataix |
| 4,968,302 A | 11/1990 | Schluter et al. |
| 4,973,168 A | 11/1990 | Chan |
| 5,051,482 A | 9/1991 | Tepic |
| 5,058,770 A | 10/1991 | Herold et al. |
| 5,067,948 A * | 11/1991 | Haber ............... A61M 5/2448 604/192 |
| 5,100,241 A | 3/1992 | Chan |
| 5,145,250 A | 9/1992 | Planck et al. |
| 5,181,909 A | 1/1993 | McFarlane |
| 5,193,907 A | 3/1993 | Faccioli et al. |
| 5,252,301 A | 10/1993 | Nilson et al. |
| 5,306,277 A | 4/1994 | Bryant et al. |
| 5,328,262 A | 7/1994 | Lidgren et al. |
| 5,330,426 A | 7/1994 | Kriesel et al. |
| 5,350,372 A | 9/1994 | Ikeda et al. |
| 5,393,497 A | 2/1995 | Haber et al. |
| 5,435,645 A | 7/1995 | Faccioli et al. |
| 5,443,182 A | 8/1995 | Tanaka et al. |
| 5,501,520 A | 3/1996 | Lidgren et al. |
| 5,531,683 A | 7/1996 | Kriesel et al. |
| 5,545,460 A | 8/1996 | Tanaka et al. |
| 5,549,380 A | 8/1996 | Lidgren et al. |
| 5,562,616 A * | 10/1996 | Haber ............... A61J 1/2089 604/191 |
| 5,564,600 A | 10/1996 | Renault |
| 5,588,745 A | 12/1996 | Tanaka et al. |
| 5,624,184 A | 4/1997 | Chan |
| 5,634,714 A | 6/1997 | Guild |
| 5,639,029 A | 6/1997 | Sundholm |
| 5,709,668 A | 1/1998 | Wacks |
| 5,779,356 A | 7/1998 | Chan |
| 5,797,678 A | 8/1998 | Murray |
| 5,826,713 A | 10/1998 | Sunago et al. |
| 5,827,262 A | 10/1998 | Neftel et al. |
| 5,876,116 A | 3/1999 | Barker et al. |
| 5,879,081 A | 3/1999 | Chordia |
| 5,934,803 A | 8/1999 | Hutter |
| 5,975,751 A | 11/1999 | Earle |
| 6,024,480 A | 2/2000 | Seaton et al. |
| 6,027,472 A | 2/2000 | Kriesel et al. |
| 6,033,105 A | 3/2000 | Barker et al. |
| 6,042,262 A | 3/2000 | Hajianpour |
| 6,099,532 A | 8/2000 | Florea |
| 6,116,773 A | 9/2000 | Murray |
| 6,120,174 A | 9/2000 | Hoag et al. |
| 6,120,490 A | 9/2000 | Neftel |
| 6,145,703 A | 11/2000 | Opperman |
| 6,174,304 B1 | 1/2001 | Weston |
| 6,176,607 B1 | 1/2001 | Hajianpour |
| 6,210,031 B1 | 4/2001 | Murray |
| 6,286,670 B1 | 9/2001 | Smith |
| 6,312,149 B1 | 11/2001 | Sjovall et al. |
| 6,379,033 B1 | 4/2002 | Murray |
| 6,387,074 B1 | 5/2002 | Horppu et al. |
| 6,406,175 B1 | 6/2002 | Marino |
| 6,425,897 B2 | 7/2002 | Overes et al. |
| 6,572,256 B2 | 6/2003 | Seaton et al. |
| 6,598,815 B2 | 7/2003 | Hsieh |
| 6,626,328 B2 | 9/2003 | Ritsche et al. |
| 6,645,171 B1 | 11/2003 | Robinson et al. |
| 6,648,499 B2 | 11/2003 | Jonsson |
| 6,655,828 B2 | 12/2003 | Vendrely et al. |
| 6,682,518 B1 | 1/2004 | Rothstein |
| 6,706,031 B2 | 3/2004 | Manera |
| 6,709,149 B1 | 3/2004 | Tepic |
| 6,736,537 B2 | 5/2004 | Coffeen et al. |
| 6,743,203 B1 | 6/2004 | Pickhard |
| 6,755,563 B2 | 6/2004 | Wahlig et al. |
| 6,796,701 B2 | 9/2004 | Wahlig et al. |
| 6,832,703 B1 | 12/2004 | Scott et al. |
| 6,871,996 B2 | 3/2005 | Jonsson |
| 6,902,543 B1 | 6/2005 | Cherif-Cheikh et al. |
| 6,940,782 B2 | 9/2005 | Matsui |
| 6,948,522 B2 | 9/2005 | Newbrough et al. |
| 6,984,063 B2 | 1/2006 | Barker et al. |
| 7,018,089 B2 | 3/2006 | Wenz et al. |
| 7,029,163 B2 | 4/2006 | Barker et al. |
| 7,073,936 B1 * | 7/2006 | Jonsson ............... B01F 11/0082 366/139 |
| 7,171,964 B2 | 2/2007 | Moore et al. |
| 7,311,436 B2 | 12/2007 | Barker et al. |

(56) References Cited

U.S. PATENT DOCUMENTS

| | | | |
|---|---|---|---|
| 7,462,164 B2 | 12/2008 | Moir | |
| 7,563,018 B2 | 7/2009 | Wilander | |
| 7,563,245 B2 | 7/2009 | Mu | |
| 7,621,887 B2 | 11/2009 | Griffiths et al. | |
| 7,661,561 B2 | 2/2010 | Ophardt et al. | |
| 7,793,655 B2 | 9/2010 | Hochrainer | |
| 7,823,751 B2 | 11/2010 | Ophardt et al. | |
| 7,938,572 B2 | 5/2011 | Lidgren et al. | |
| 7,959,349 B2 | 6/2011 | Sattig et al. | |
| 7,980,754 B2 | 7/2011 | Wilander et al. | |
| 8,128,275 B2 | 3/2012 | Axelsson et al. | |
| 8,128,276 B2 | 3/2012 | Axelsson et al. | |
| 8,132,959 B2 | 3/2012 | Smit | |
| 8,256,949 B2 | 9/2012 | Melsheimer et al. | |
| 9,186,635 B2 * | 11/2015 | Bielenstein | B01F 7/007 |
| 9,480,955 B2 * | 11/2016 | Sasaki | B01F 15/0206 |
| 2002/0123739 A1 | 9/2002 | Haacke et al. | |
| 2003/0155381 A1 | 8/2003 | Chan | |
| 2004/0066706 A1 * | 4/2004 | Barker | A61B 17/8822 366/139 |
| 2005/0113762 A1 | 5/2005 | Kay et al. | |
| 2005/0228396 A1 | 10/2005 | Jonsson | |
| 2006/0101925 A1 | 5/2006 | Peng et al. | |
| 2009/0180349 A1 | 7/2009 | Barker et al. | |
| 2009/0264891 A1 | 10/2009 | Bogert et al. | |
| 2010/0046315 A1 | 2/2010 | Merkhan et al. | |
| 2012/0325367 A1 * | 12/2012 | Mathys | A61B 17/8833 141/18 |
| 2016/0045242 A1 * | 2/2016 | Bielenstein | B01F 7/007 366/139 |
| 2017/0239631 A1 * | 8/2017 | Sattig | B01F 15/0212 |

FOREIGN PATENT DOCUMENTS

| | | |
|---|---|---|
| DE | 60126156 T2 | 10/2007 |
| DE | 102007041666 A1 | 4/2009 |
| EP | 0380867 A1 | 8/1990 |
| EP | 0493363 A2 | 7/1992 |
| EP | 0674888 A1 | 10/1995 |
| EP | 0694498 A1 | 1/1996 |
| EP | 0725674 A1 | 8/1996 |
| EP | 0919215 A1 | 6/1999 |
| EP | 1005900 A2 | 6/2000 |
| EP | 1020167 A2 | 7/2000 |
| EP | 1031333 A1 | 8/2000 |
| EP | 1395208 B1 | 1/2007 |
| EP | 1741413 A1 | 1/2007 |
| EP | 1886648 A1 | 2/2008 |
| EP | 1920738 A2 | 5/2008 |
| FR | 1413976 A | 10/1965 |
| WO | 9013264 A1 | 11/1990 |
| WO | 9300366 A1 | 1/1993 |
| WO | 9302322 A1 | 2/1993 |
| WO | 9322041 A1 | 11/1993 |
| WO | 9400415 A1 | 1/1994 |
| WO | 9426403 A1 | 11/1994 |
| WO | 9509641 A1 | 4/1995 |
| WO | 9607472 A1 | 3/1996 |
| WO | 9718031 A1 | 5/1997 |
| WO | 9967015 A1 | 12/1999 |
| WO | 0035506 A1 | 6/2000 |
| WO | 0043116 A1 | 7/2000 |
| WO | 03031042 A1 | 4/2003 |
| WO | 2010105807 A1 | 9/2010 |

OTHER PUBLICATIONS

International Preliminary Report on Patentabilty for Application No. PCT/EP2010/001665 English Translation Undated 5 pages.
Third Party Observation for Application No. EP20100710798.
International Search Report dated Apr. 8, 2012 in PCT/EP2012/003762.
Written Opinion dated Apr. 8, 2012 in PCT/EP2012/003762.

* cited by examiner

VACUUM MIXING DEVICE FOR BONE CEMENT AND METHOD FOR MIXING BONE CEMENT IN SAID DEVICE

CROSS REFERENCE TO RELATED APPLICATIONS

The present application is a continuation of U.S. patent application Ser. No. 13/257,031 filed Sep. 16, 2011, now U.S. Pat. No. 9,186,635, which application is a national phase entry under 35 U.S.C. § 371 of International Application No. PCT/EP2010/001665 filed Mar. 17, 2010, published as International Publication No. WO 2010/105807 A1, which claims priority from German Patent Application No. 10 2009 013 211.2 filed Mar. 17, 2009, the disclosures of which are incorporated herein by reference.

FIELD OF THE INVENTION

The invention relates to a vacuum mixing device for bone cement and to a method for producing bone cement.

BACKGROUND OF THE INVENTION

Mixing devices for bone cement are known.

Such a generic mixing device is shown, for example, in the applicant's German patent application DE 10 2007 041 666 A1. When preparing bone cement, a powder, in particular a PMMA powder, is typically mixed with a liquid monomer. Vacuum mixing systems are known so as to avoid the formation of bubbles and/or to prevent harmful gaseous substances that develop during preparation from escaping into the environment. These are systems in which the mixing container comprises a connection for a vacuum hose, via which the container is placed under a vacuum during the mixing process.

Known conventional system often require relatively complicated operation, in which the user must perform several steps associated with sources of errors. In particular, it is important to precisely adhere to the predefined mixing ratio between the monomer and powder.

For this purpose, for example, systems are known in which the monomer is suctioned into the mixing container based on a vacuum that is present in the mixing container. Such conventional systems generally have a valve through which air can flow into the monomer container, so that the existing liquid is completely discharged from the monomer container. Such a system is described, for example, in the European patent specification EP 0 725 647 B1.

The disadvantage of such a system is that the bone cement can become contaminated with microbes from the ambient air, in particular if this system is not operated in a sterile environment.

SUMMARY OF THE INVENTION

In contrast, it is the object of the invention to at least reduce the aforementioned disadvantages of the prior art.

It is in particular an object of the invention to be able to provide a vacuum mixing system for bone cement which enables simple and safe handling.

The object of the invention is already achieved by a vacuum mixing device and by a method for preparing bone cement according to any one of the independent claims.

Preferred embodiments and refinements of the invention are disclosed in the respective dependent claims.

The invention relates first to a vacuum mixing device for bone cement, comprising a mixing chamber in which a monomer can be mixed with the powder. So as to avoid the formation of bubbles and prevent harmful gases from escaping, the mixing chamber can be connected to a vacuum source, in particular to a vacuum pump.

The vacuum mixing device moreover comprises a monomer container, which can be coupled to the mixing chamber. The monomer is preferably already contained in the monomer container upon delivery of the vacuum mixing device and thus does not need to be withdrawn from a separate container and added. The term "can be coupled" means that the vacuum mixing device comprises means for forming a passage in which the monomer flows from the monomer container into the mixing container connected to the monomer container.

According to the invention, the closed monomer container is filled partially with a gas, the volume of which is calculated such that, when a vacuum is present, the monomer is displaced by the gas and thus flows into the mixing container.

The monomer container is preferably not subject to overpressure, but instead has, for example, substantially atmospheric pressure. This enables a simpler design of the container, and the monomer is prevented from escaping in an uncontrolled manner in the event of damage.

If the monomer container is, for example, under atmospheric pressure and a vacuum source is applied that generates a vacuum of approximately 0.5 bar in the mixing container, the gas volume in the monomer container must consequently account for at least half the volume.

The invention enables an entirely closed design of the vacuum mixing device, so that there is no risk during mixing for microbes from the air that is suctioned in to contaminate the bone cement.

The gas that is used can be air in the simplest case, but other gases, in particular those that form a preserving protective atmosphere, are also conceivable. Nitrogen or a noble gas may also be used, for example.

In a preferred embodiment of the invention, the gas volume is so large that the monomer flows into the mixing container up to a predefined fill level, or fully, when a vacuum is present.

A predefined residual fill quantity can be determined, for example, by the height of the cannula protruding into the monomer container during mixing. Depending on the embodiment, complete emptying of the monomer container is also possible.

In this embodiment of the invention, the amount of liquid to be dispensed can be exactly gauged, because the monomer container is emptied fully automatically and the user has no influence on the residual quantity remaining in the monomer container, as is the case, for example, with filling using a syringe.

In a preferred embodiment of the invention, at least 20%, and more preferably 40%, of the volume of the monomer container is filled with the gas.

In a refinement of the invention, the monomer container has a membrane and the vacuum mixing device comprises a piercing cannula, by means of which the membrane can be pierced and the monomer thus flows via the cannula into the mixing container.

This embodiment of the invention enables, in particular, the use of commercially available monomer vials made of glass, which are provided with a membrane. The monomer is thus stored in a safe and sterile manner in the monomer vial.

The invention further relates to a vacuum mixing device which comprises a mixing container, which can be connected to a vacuum source. The vacuum mixing device comprises a monomer container, which can be coupled to the mixing container.

So as to enable a particularly simple design of the device, the monomer container is disposed on a handle, which can also be used to actuate a mixing blade in the mixing chamber, wherein the monomer can be mixed manually with the powder using this mixing blade by moving the mixing blade up and down.

A rod is connected to the handle so as to move the mixing blade.

According to the invention, the rod is guided in a plate, which can be used as a plunger for expelling the bone cement after the bone cement has been prepared.

The rod preferably comprises a channel, which is used to join the mixing container to the monomer container, which is to say to allow the monomer to flow into the mixing container.

The invention enables a design of a vacuum mixing device which is particularly easy to handle, wherein, as in a preferred embodiment of the invention, the handle together with the monomer container can be broken off after the mixing process is complete and the mixing container is employed as a kind of cartridge in a dosing gun. To this end, the plate, which initially serves to guide the rod, is used as a plunger for pushing the bone cement out of the mixing container.

According to one embodiment of the invention, the monomer container comprises a monomer vial disposed in a receiving unit. This embodiment of the invention makes is possible, among others, to use commercially available monomer vials and, as in a preferred embodiment of the invention, the remaining monomer container does not have to be designed to be vacuum-sealed because, for example, a membrane that is present on the monomer vial can served as a sealing element.

In a special embodiment of the invention, the receiving unit is designed to be telescoping. A monomer vial held in the receiving unit can thus be pushed onto a cannula, for example.

The invention further relates to a vacuum mixing device comprising a mixing chamber and a monomer container, which can be coupled to the mixing chamber.

According to the invention, the monomer container engages in the coupled state and is preferably locked in this engaged state.

Thus, the user cannot break the connection between the monomer container and mixing container once it has been established. The monomer thus enters the mixing container completely, and there is no risk of the user separating the monomer container as a result of improper use before the container is emptied.

In a refinement of the invention, the vacuum mixing device comprises a safety bolt which, upon removal, releases the monomer container for movement into the coupled state. Such a safety container prevents accidental actuation of the device.

The vacuum mixing device preferably comprises means for blocking reinsertion of the removed safety bolt. Once the safety bolt has been pulled, it thus also serves as a tamper-proofing element, making it immediately apparent if the vacuum mixing device has been previously used and therefore consumed.

The invention further relates to a method for preparing bone cement. To this end, a monomer is mixed with a powder in a mixing container and a vacuum is applied to the mixing container, at least while mixing.

According to the invention, when the vacuum is present, the monomer is pressed out of the monomer container into the mixing container by a gas that expands as a result of the vacuum.

The method makes a fully closed design of the mixing system possible.

During preparation, the mixing cup and monomer container are thus preferably protected from the penetration of outside air.

In one embodiment of the invention, the monomer container is pierced by means of a cannula and the monomer is conducted via the cannula into the mixing container.

In this connected position, the monomer container engages such that the inflow of monomer can no longer be interrupted.

In a refinement of the invention, the monomer container is separated from the mixing container after the bone cement has been prepared, and the mixing container is used as a cartridge for a dosing gun.

BRIEF DESCRIPTION OF THE DRAWINGS

The invention will be described in more detail hereafter with reference to the drawings, these being FIG. 1 to FIG. 6, which show schematic views of embodiments of the invention.

The entire vacuum mixing device will be described in more detail with reference to FIGS. 5 and 6.

DETAILED DESCRIPTION

Figure 1:
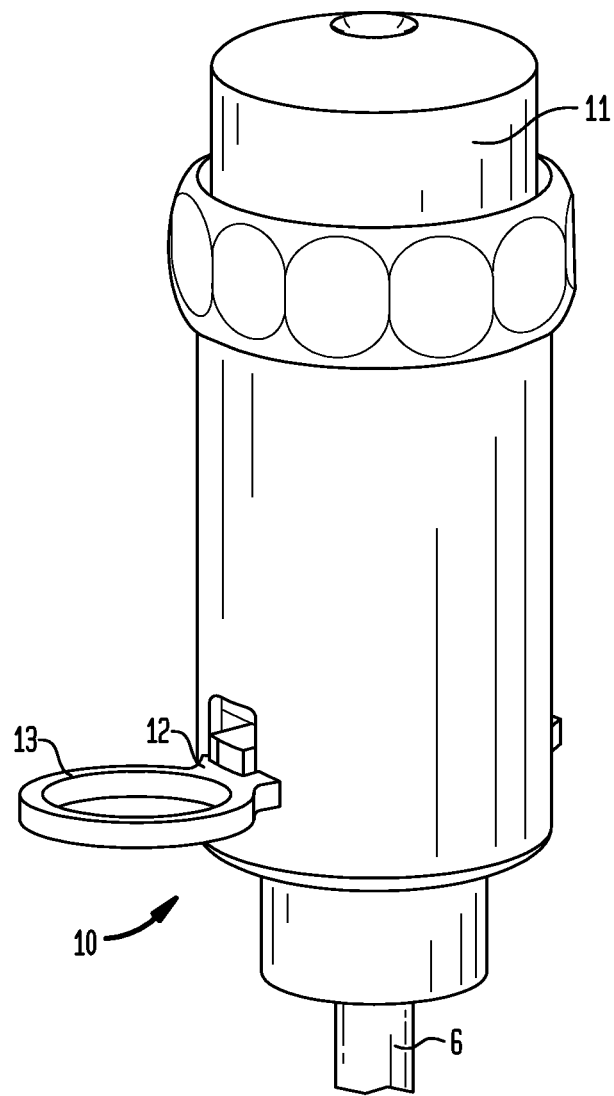
FIG. 1 to FIG. 4 show schematic views of an exemplary embodiment of a handle comprising a monomer container for a vacuum mixing device according to the invention.

FIG. 1 is a schematic view of a monomer container 10 designed as a handle for a mixing blade (not shown). The monomer container 10 has a substantially cylindrical shape and comprises an actuating button 11 for releasing the monomer (not shown).

In order to be able to press the actuating button 11, a safety bolt 12 having a handle 13, which forms a finger hole, is provided, which must be removed first.

After the safety bolt 12 has been removed, the actuating button 11 can be pressed and the monomer flows, with a vacuum in the mixing container, into the mixing container (not shown) via a channel (not shown) that is embedded in the rod 6.

Figure 2:
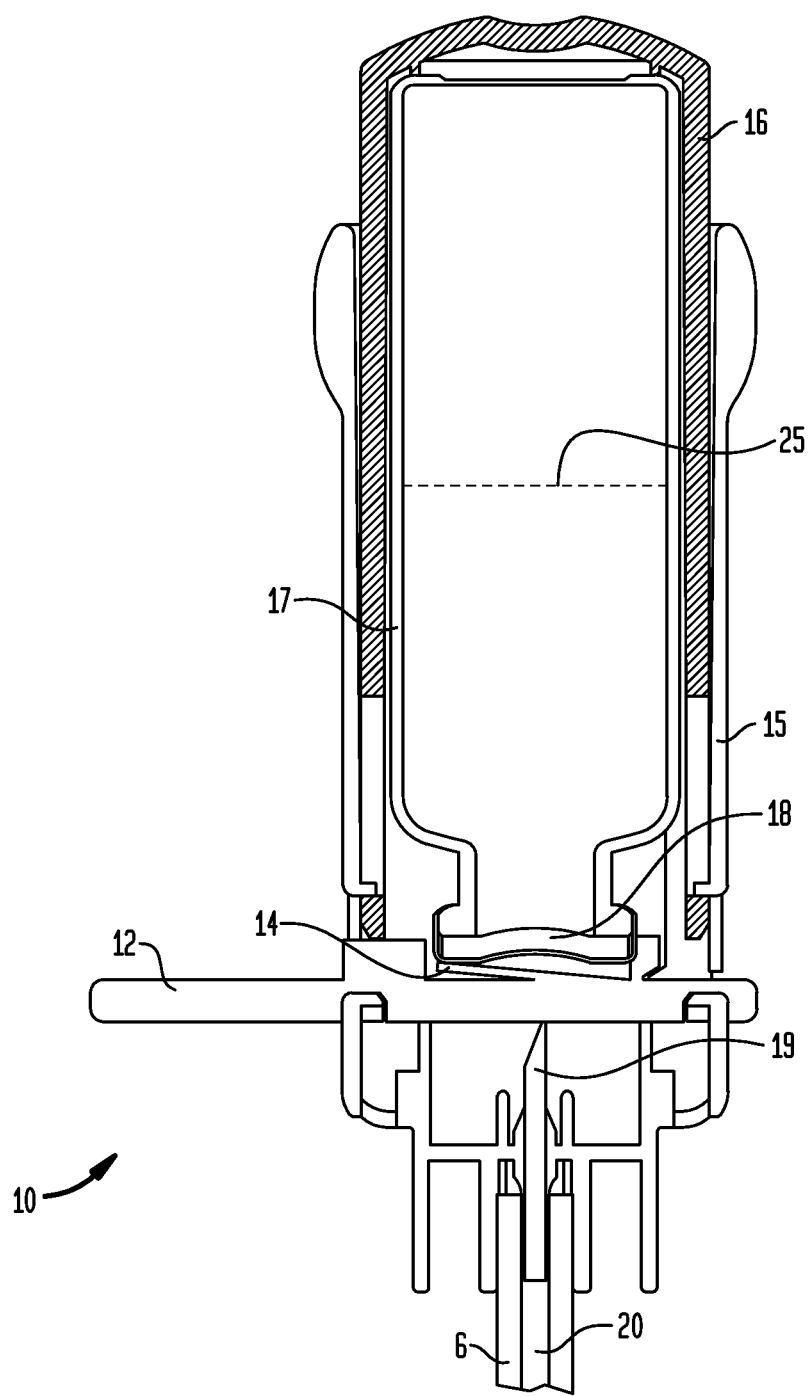

FIG. 2 shows a sectional view of the monomer container 10 shown in FIG. 1 in a starting state, which is to say prior to use.

The monomer container 10 comprises a lower housing part 15 and an upper housing part 16, which is also designed as the actuating button 11.

The housing parts 15, 16 are used to accommodate a commercially available monomer vial 17 made of glass, which is sealed with a membrane 18.

The monomer fills the monomer vial 17 approximately half in this exemplary embodiment. The fill level is predefined by the line 25.

The monomer container 10 further comprises a cannula 19, which is connected to a channel 20 that is embedded in the rod 6.

The cannula 19 and the membrane 18 of the monomer vial 17 are held apart from each other by the safety bolt 12 so that accidental actuation is not possible.

The safety bolt 12 comprises a spring-loaded tongue so as to compensate for manufacturing tolerances of the monomer vial 17.

As soon as the safety bolt 12 has been pulled out, the monomer vial 17 slides into a position in which the safety bolt 12 cannot be re-inserted.

Figure 3:
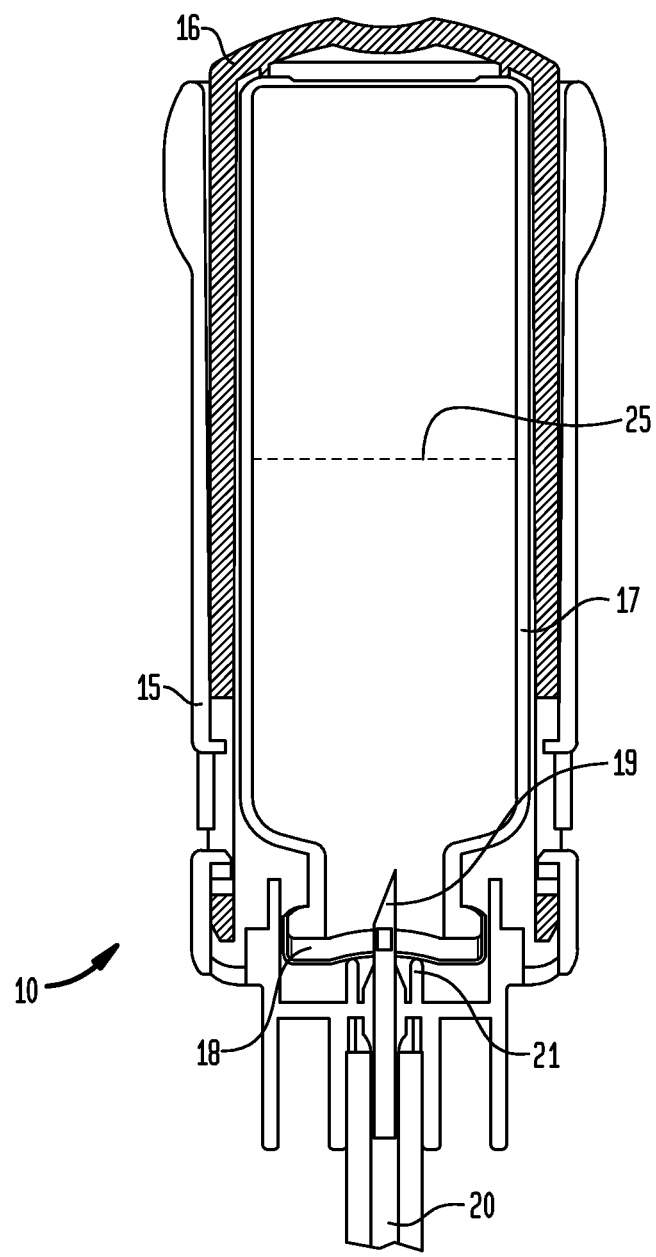

FIG. 3 shows a sectional view of the monomer container 10 after actuation.

When the actuating button is pressed, the upper housing part 16 and the lower housing part 15 are pushed inside each other, whereby the monomer vial 17 is pushed onto the cannula 19 which pierces the membrane 18 so that the monomer can enter the mixing container (not shown) via the channel 20.

Because of the air volume that is present above the fill level 25 and the vacuum that is present in the mixing container, the monomer is emptied to a low residual fill level, which is predefined by the position of the cannula 19.

In order to define an exact position of the cannula 19 relative to the monomer vial 17, a ring 21 is provided in the lower housing part, with the monomer vial 17 being seated on this ring in the actuated state.

Figure 4:
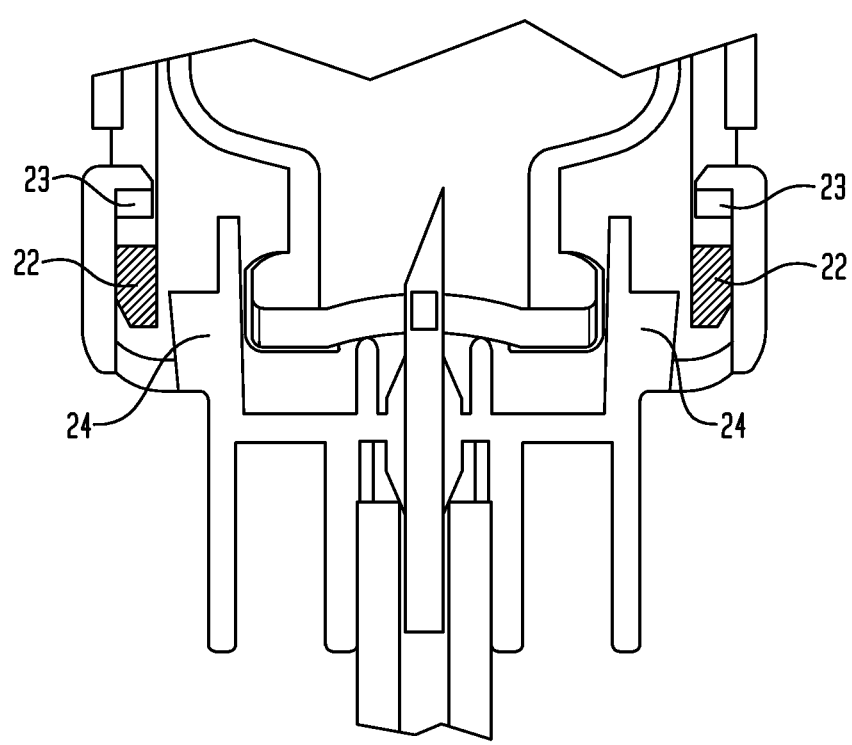

FIG. 4 shows a detail view of the head of the monomer container shown in FIG. 3. The engagement of the monomer container will be described in more detail with reference to this figure.

The upper housing part comprises catch hooks 22, which in the actuated state engage beneath catch lugs 23 of the lower housing part. For this purpose, the catch hooks 22 are beveled. It is not possible to pull them apart after engagement.

So as to further increase the protection from manipulation, ribs 24 are provided on the lower housing part, which substantially prevent the use of a tool to push the catch hooks inward from beneath and thus return the monomer vial to the original position.

Figure 5:
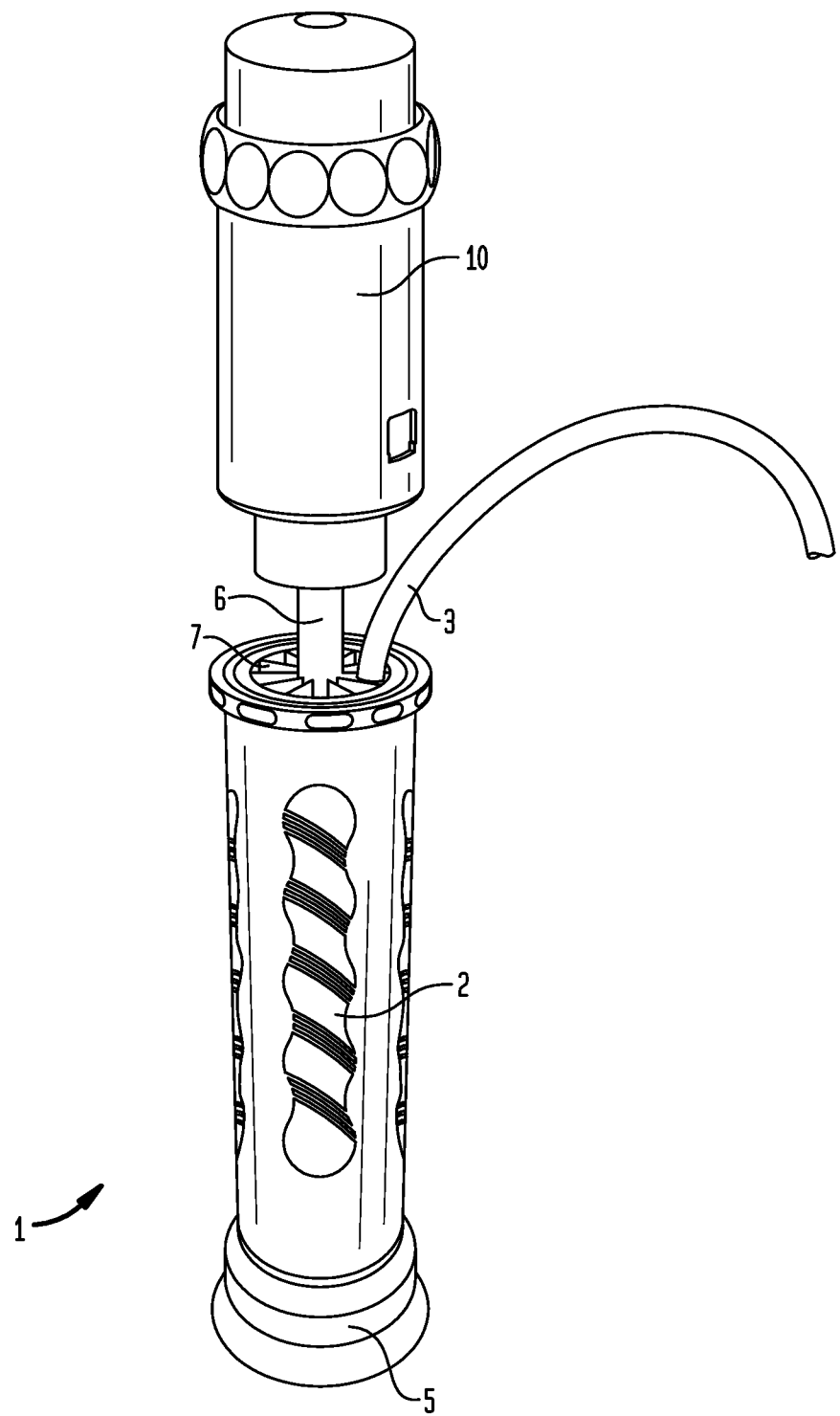

FIG. 5 is a schematic view of the entire vacuum mixing device.

The monomer container 10 is designed as a handle, which is connected via a rod 6 to a mixing blade (not shown).

The mixing container 2 is preferably already prefilled with the powder.

In order to ensure that the powder does not enter the rod 6, a filter, and more particularly a filter plate, is provided (not shown) at the lower end of the rod.

When the vacuum mixing device 1 is used, a vacuum pump is connected to a vacuum connection 3 on the mixing container 2. A nonwoven fabric (not shown) that is embedded in the vacuum connection prevents bone cement from escaping.

A withdrawal opening, which initially is still screwed to a base 5, is located at the bottom of the mixing container 2.

The user (not shown) first connects the mixing container 2 to the vacuum.

Then, he pulls the safety bolt and pushes the actuating button 11 of the monomer container.

Because of the vacuum, the monomer (not shown) is displaced by the gas trapped in the monomer container 10 and flows via the rod 6 into the mixing container 2. To this end, the rod 6 comprises lateral openings above the mixing blades (not shown).

The user then uses the monomer container 10 as a handle so as to move the mixing blades (not shown) in the mixing container 2 and thus prepare the bone cement.

Thereafter, the user pulls the mixing blade all the way to the top and completely breaks off the rod 6 together with the monomer container 10 at a predetermined breaking point.

Moreover, the user unscrews the base 5, whereby the withdrawal opening is uncovered.

The mixing container 2 can now be utilized as a cartridge for a dosing gun (not shown). To this end, the cover 7 of the mixing container 2, in which the rod 6 is also guided, serves as a plunger. The cover 7 can, for this purpose, be connected to the remaining mixing container 2 so that it detaches at a particular force and can then be pushed forward. The cover can, for example, be pressed into a groove of the cylindrical housing of the mixing container 2.

Figure 6:
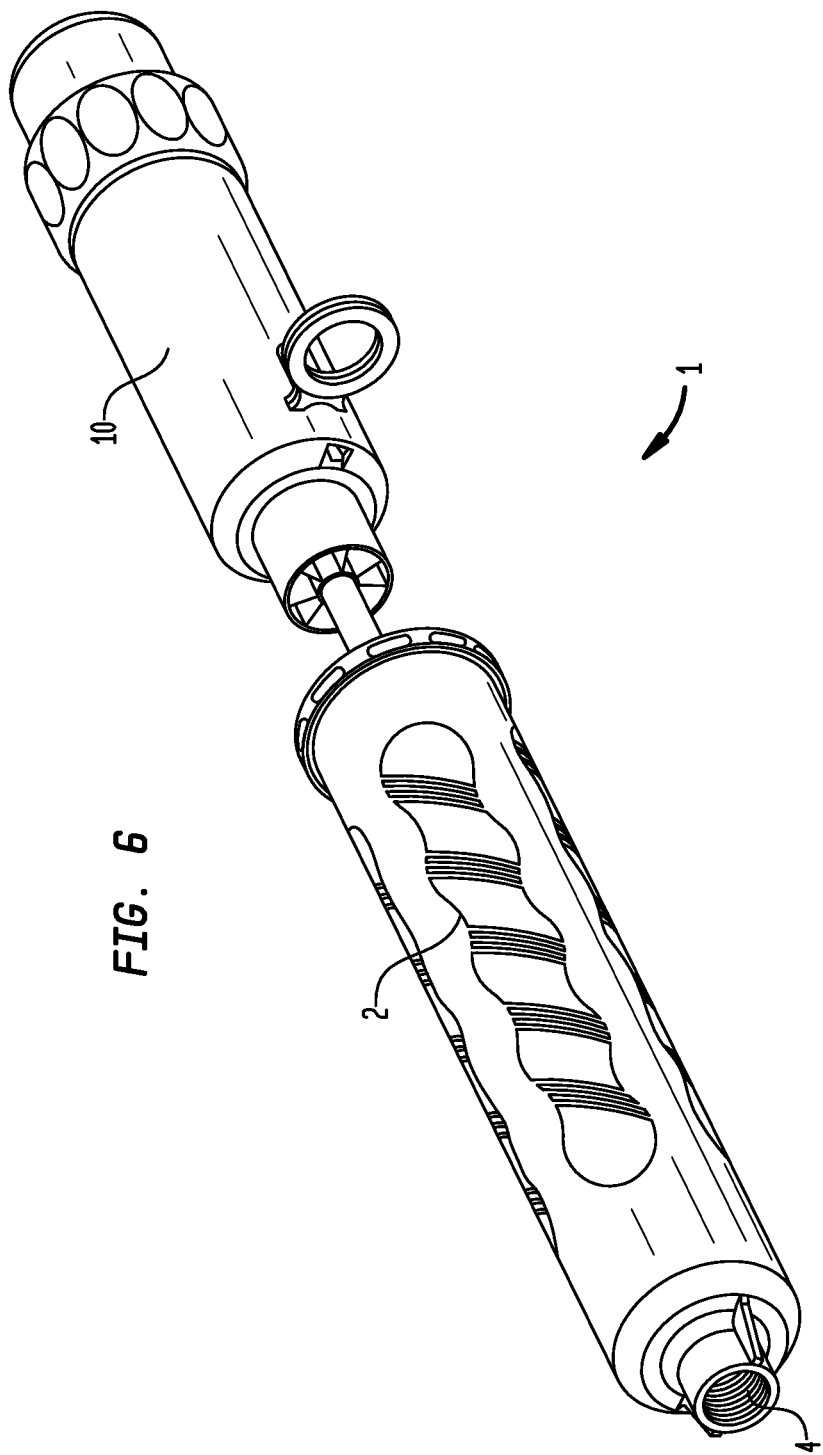

FIG. 6 shows a further perspective view of a vacuum mixing device 1. In this view, the base (5 in FIG. 5) has already been unscrewed, so that the withdrawal opening 4 is visible.

The invention enables particularly simple and safe handling of bone cement.

The invention is, of course, not limited to a combination of the aforedescribed characteristics, but a person skilled in the art can combine all the features to the extent this is expedient.

LIST OF REFERENCE NUMERALS

1 Vacuum mixing device
2 Mixing container
3 Vacuum connection
4 Withdrawal opening
5 Base
6 Rod
7 Cover
10 Monomer container
11 Actuating button
12 Safety bolt
13 Handle
14 Tongue
15 Lower housing part
16 Upper housing part
17 Monomer vial
18 Membrane
19 Cannula
20 Channel
21 Ring
22 Catch hook
23 Catch lug
24 Rib
25 Fill level

The invention claimed is:

1. A mixing device for preparing bone cement, comprising:
   a mixing container;
   a monomer container attached to the mixing container and having first and second telescoping parts, the monomer container being moveable relative to the mixing container,
   wherein one of the first and second telescoping parts of the monomer container includes at least one catch hook and the other of the first and second telescoping parts of the monomer container includes at least one catch lug for engagement with the respective at least one catch hook such that the monomer container is locked in position relative to the mixing container.

2. The mixing device of claim 1, further comprising a pin for engagement with the monomer container, the pin being disengageable from and removable from the monomer container,
   wherein, when the pin is engaged with the monomer container, the first telescoping part of the monomer container does not move relative to the second telescoping part of the monomer container, and, upon removal of the pin, the first telescoping part of the monomer container moves relative to the second telescoping part of the monomer container.

3. The mixing device of claim 2, further comprising a monomer vial disposed in the monomer container, wherein upon removal of the pin, the monomer vial slides toward the mixing container and prevents reinsertion of the pin.

4. The mixing device of claim 2, further comprising a monomer vial disposed in the monomer container,
wherein the pin includes a shaft and a deflectable tongue extending from the shaft, and
wherein, when the pin is engaged with the monomer container, the monomer container rests on the tongue.

5. The mixing device of claim 2, further comprising a cannula attached to the monomer container and configured to pierce a monomer vial when the monomer vial is disposed in the monomer container, wherein when the pin is engaged with the monomer container and the monomer vial is disposed in the monomer container, the pin extends across the monomer container to separate the cannula from the monomer vial.

6. The mixing device of claim 2, wherein the mixing container is connectable to a vacuum source, the mixing device further comprising:
a monomer vial disposed in the monomer container and filled at least partially with a volume of gas; and
a cannula attached to the monomer container and configured to pierce the monomer vial,
wherein when a vacuum is present in the mixing container and the piercing cannula pierces the monomer container, the monomer flows from the monomer container into the mixing container to at least a predefined fill level.

7. The mixing device of claim 6, wherein the at least 20% of the volume of the monomer container is filled with the volume of gas.

8. The mixing device of claim 6, wherein the at least 40% of the volume of the monomer container is filled with the volume of gas.

9. The mixing device of claim 1, wherein the monomer container includes a rod, the monomer container being attached to the mixing container via the rod.

10. The mixing device of claim 9, wherein the monomer container is configured to receive a monomer vial and a channel is disposed in the rod, and wherein monomer from the monomer vial is receivable in the mixing container through the rod.

11. The mixing device of claim 10, further comprising a cannula attached to the monomer container and received in a channel of the rod, the cannula being configured to pierce the monomer vial when the monomer vial is received in the monomer container.

12. The mixing device of claim 9, wherein the mixing container includes a plate, and wherein the rod of the monomer container is guided through the plate, the plate being detachable such that the plate is moveable to expel prepared bone cement.

13. A mixing device for preparing bone cement, comprising:
a rod;
a mixing container;
a monomer container attached to the mixing container via the rod and including first and second telescoping parts, the monomer container and the rod being moveable relative to the mixing container;
a cannula attached to the monomer container and having an end received in a channel of the rod, the cannula being configured to pierce a monomer vial when the monomer vial is disposed in the monomer container, wherein when the monomer vial is pierced, monomer flows via the cannula into the mixing container; and
a pin for engagement with the monomer container, the pin being disengageable from and removable from the monomer container, wherein, when the pin is engaged with the monomer container, the first telescoping part of the monomer container does not move relative to the second telescoping part of the monomer container, and, upon removal of the pin, the first telescoping part of the monomer container moves relative to the second telescoping part of the monomer container.

14. The mixing device of claim 13, wherein the monomer vial is disposable between the first and second telescoping parts when the monomer vial is disposed in the monomer container and such that when the first telescoping part is telescoped relative to the second telescoping part from a first position to a second position with the monomer vial is disposed in the monomer container, the monomer vial is pushed onto the cannula.

15. The mixing device of claim 13, further comprising the monomer vial disposed in the monomer container,
wherein the pin includes a shaft and a deflectable tongue extending from the shaft, and
wherein, when the pin is engaged with the monomer container, the monomer container rests on the tongue.

16. The mixing device of claim 13, wherein when the pin is engaged with the monomer container and the monomer vial is disposed in the monomer container, the pin extends across the monomer container to separate the cannula from the monomer vial.

17. The mixing device of claim 13, wherein when the monomer vial is pierced, monomer flows via the cannula into the mixing container, wherein the mixing container includes a plate, and wherein the rod of the monomer container is guided through the plate, the plate being detachable such that the plate is moveable to expel prepared bone cement.

18. A mixing device for preparing bone cement, comprising:
a mixing container;
a monomer container attached to the mixing container and having first and second telescoping parts, the monomer container being moveable relative to the mixing container; and
a pin for engagement with the monomer container, the pin being disengageable from and removable from the monomer container, wherein, when the pin is engaged with the monomer container, the first telescoping part of the monomer container is prevented from moving relative to the second telescoping part of the monomer container, and, upon removal of the pin, the first telescoping part of the monomer container slides relative to the second telescoping part of the monomer container.

19. A mixing device for preparing bone cement, comprising:
a rod;
a mixing container;
a monomer container attached to the mixing container via the rod, the monomer container and the rod being moveable relative to the mixing container; and
a cannula attached to the monomer container and having an end received in a channel of the rod, the cannula being configured to pierce a monomer vial when the monomer vial is disposed in the monomer container, wherein when the monomer vial is pierced, monomer flows via the cannula into the mixing container, wherein the mixing container includes a plate, and wherein the rod of the monomer container is guided through the plate, the plate being detachable such that the plate is moveable to expel prepared bone cement.

20. A mixing device for preparing bone cement, comprising:

a rod;

a mixing container;

a monomer container attached to the mixing container via the rod, the monomer container and the rod being moveable relative to the mixing container;

a monomer vial disposed in the monomer container; and a cannula attached to the monomer container and having an end received in a channel of the rod, the cannula being configured to pierce the monomer vial, wherein when the monomer vial is pierced, monomer flows via the cannula into the mixing container, wherein the mixing container is connectable to a vacuum source, the monomer vial being filled at least partially with a volume of gas, and wherein when a vacuum is present in the mixing container and the cannula pierces the monomer vial, the monomer flows from the monomer container into the mixing container to at least a predefined fill level.

* * * * *